(12) United States Patent
Nowottny et al.

(10) Patent No.: US 11,083,673 B2
(45) Date of Patent: *Aug. 10, 2021

(54) HYDROGEN PEROXIDE FORMULATIONS IN BARRIER LAYER FILMS WITH A SIOX LAYER

(71) Applicant: Henkel AG & Co. KGaA, Duesseldorf (DE)

(72) Inventors: Marc Nowottny, Moenchengladbach (DE); Torsten Lechner, Langenfeld (DE); Wolfgang Barthel, Langenfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/767,776

(22) PCT Filed: Nov. 22, 2018

(86) PCT No.: PCT/EP2018/082262
§ 371 (c)(1),
(2) Date: May 28, 2020

(87) PCT Pub. No.: WO2019/120862
PCT Pub. Date: Jun. 27, 2019

(65) Prior Publication Data
US 2020/0360246 A1 Nov. 19, 2020

(30) Foreign Application Priority Data
Dec. 18, 2017 (DE) .................. 10 2017 223 025.8

(51) Int. Cl.
| | | |
|---|---|---|
| *A61Q 5/08* | (2006.01) | |
| *A61K 8/22* | (2006.01) | |
| *A45D 37/00* | (2006.01) | |
| *A61K 8/34* | (2006.01) | |
| *A61K 8/39* | (2006.01) | |
| *A61K 8/46* | (2006.01) | |
| *A61K 8/81* | (2006.01) | |
| *A61Q 5/10* | (2006.01) | |
| *B32B 7/12* | (2006.01) | |
| *B32B 27/08* | (2006.01) | |
| *B32B 27/32* | (2006.01) | |
| *B32B 27/36* | (2006.01) | |

(52) U.S. Cl.
CPC .............. *A61K 8/22* (2013.01); *A45D 37/00* (2013.01); *A61K 8/342* (2013.01); *A61K 8/39* (2013.01); *A61K 8/463* (2013.01); *A61K 8/8147* (2013.01); *A61Q 5/10* (2013.01); *B32B 7/12* (2013.01); *B32B 27/08* (2013.01); *B32B 27/32* (2013.01); *B32B 27/36* (2013.01); *A61K 2800/48* (2013.01); *A61K 2800/596* (2013.01); *A61K 2800/87* (2013.01); *B32B 2250/03* (2013.01); *B32B 2250/24* (2013.01); *B32B 2255/10* (2013.01); *B32B 2255/20* (2013.01); *B32B 2307/7244* (2013.01); *B32B 2307/7246* (2013.01); *B32B 2553/00* (2013.01)

(58) Field of Classification Search
CPC . A61Q 5/08; A61K 8/22; A61K 8/342; A61K 2800/87; A61K 2800/596; A45D 37/00; B32B 27/08; B32B 27/32; B32B 27/36; B32B 2250/24; B65D 75/26; C08J 5/18; C08J 2323/06
USPC ........................................................ 424/62
See application file for complete search history.

(56) References Cited

U.S. PATENT DOCUMENTS

| | | |
|---|---|---|
| 6,503,634 B1 | 1/2003 | Utz et al. |
| 2013/0074863 A1 | 3/2013 | Kleen et al. |
| 2017/0150800 A1* | 6/2017 | Mueller ................. A61K 8/368 |
| 2017/0354833 A1 | 12/2017 | Mueller |

FOREIGN PATENT DOCUMENTS

| | | |
|---|---|---|
| DE | 102010029206 A1 | 11/2011 |
| DE | 102015223838 A1 | 6/2017 |
| EP | 0792846 A1 | 9/1997 |
| EP | 1036813 A1 | 9/2000 |
| EP | 1541340 A1 | 6/2005 |
| EP | 2371539 A1 | 10/2011 |
| WO | 03089330 A1 | 10/2003 |
| WO | 2016096284 A1 | 6/2016 |

OTHER PUBLICATIONS

EPO, International Search Report issued in International Application No. PCT/EP2018/082262, dated Feb. 12, 2019.

* cited by examiner

*Primary Examiner* — Eisa B Elhilo
(74) *Attorney, Agent, or Firm* — Lorenz & Kopf, LLP

(57) ABSTRACT

The present disclosure concerns a cosmetic product for modifying the natural colour of keratinous fibres, in particular human hair, comprising at least one packaging (VP) and a cosmetic composition (KM) contained in this packaging (VP). The packaging is made of a multilayer film (F) containing at least two polymer layers (P1) and (P2) and at least one barrier layer (BS). The cosmetic composition comprises at least one oxidizing agent, at least one $C_8$-$C_{30}$-alcohol, at least one specific anionic surfactant, at least one non-ionic surfactant and at least one acrylic acid-based thickener. The use of the packaging (VP) in combination with the cosmetic composition (KM) surprisingly does not lead to an inflation of the packaging or an excessive loss of water of the agent (KM) during storage.

19 Claims, No Drawings

HYDROGEN PEROXIDE FORMULATIONS IN BARRIER LAYER FILMS WITH A SIOX LAYER

CROSS-REFERENCE TO RELATED APPLICATION

This application is a U.S. National-Stage entry under 35 U.S.C. § 371 based on International Application No. PCT/EP2018/082262, filed Nov. 22, 2018, which was published under PCT Article 21(2) and which claims priority to German Application No. 10 2017 223 025.8, filed Dec. 18, 2017, which are all hereby incorporated in their entirety by reference.

TECHNICAL FIELD

The present disclosure is in the field of cosmetics and relates to a product for the oxidative color change of keratin fibres, in particular human hair, which comprises an oxidant-containing composition packed in a packaging. The oxidizing agent-containing composition contains at least one $C_8$-$C_{30}$-Alcohol, at least one special anionic surfactant, at least one non-ionic surfactant and at least one acrylic acid polymer as a thickener. The packaging is made from a special multi-layer film composite system, the wall of which comprises at least two polymer layers and a barrier layer. The barrier layer has a passage barrier effect for gases and water vapour. The barrier layer comprises of silicon oxide.

BACKGROUND

Changing the colour of keratin fibres, especially hair, is an important area of modern cosmetics. As a result, the appearance of the hair can be adapted both to current fashion trends and to the individual wishes of the individual. The expert knows different possibilities for changing the hair colour. The hair colour can be changed temporarily by using direct dye. Here, already fully formed dyes from the dye diffuse into the hair fibre. The dyeing with direct dyes is associated with little damage to the hair, but a disadvantage is the short shelf life and the quick washability of the dyeings obtained with direct dyes.

If the consumer desires a long-lasting colour result or a shade that is lighter than his original hair colour, oxidative colour change agents are therefore usually used. So-called oxidation dyes are used for permanent, intensive dyeings with appropriate fastness properties. Such colourants usually contain oxidation dye precursors, so-called developer components and coupler components, which form the actual dyes with one another under the influence of oxidizing agents—usually hydrogen peroxide. Oxidation dyes are exemplified by excellent, long-lasting dyeing results.

Oxidative colour change agents usually come on the market in the form of two-component agents, in which two different preparations are packaged separately in two separate packages and are only mixed with one another shortly before use. The first preparation is a formulation which is generally acidic for stability reasons and which contains, for example, hydrogen peroxide in concentrations of from about 1.5 to about 12% by weight as the oxidizing agent. The oxidizing agent formulation is usually in the form of an emulsion or dispersion and is usually provided in a plastic bottle with a resealable outlet opening (developer bottle).

This oxidizing agent formulation is mixed with a second preparation prior to use. This second preparation is an alkaline formulation which is often in the form of a cream or a gel and which, if a color change is also desired at the same time as the lightening, also contains at least one oxidation dye precursor. This second preparation can be provided, for example, in the form of a tube or in the form of a plastic or glass container.

In the conventional application form described above, the second preparation, which contains the alkalising agent and/or the oxidation dye precursors, is transferred from the tube or the container into the developer bottle and then mixed by shaking with the hydrogen peroxide preparation already present in the developer bottle. In this way, the application mixture is produced in the developer bottle. It is then applied to the hair via a small nozzle or outlet opening on the head of the developer bottle. The nozzle or opening is opened after shaking and the application mixture can be removed by pressing the flexible developer bottle.

The use of the developer bottle requires a certain routine from the user, so that some users prefer to prepare the application mixture in a mixing bowl and to apply it using a brush.

When preparing the application mixture in a bowl, both components—the first preparation containing the oxidizing agent and the second preparation with alkalising agent and/or oxidation dye precursors—are transferred completely into a bowl or similar vessel and stirred there, for example with the aid of a brush. The application mixture is then removed from the mixing bowl using the brush. In this form of application, the use of a voluminous and expensive developer bottle is not necessary, and the search continues for inexpensive and material-saving packaging forms for the oxidant preparation.

In this context, packaging in the form of bags or pouches, which are usually made of plastic films or metal films, is an inexpensive form of packaging with low material consumption.

Such packaging can be produced, for example, by gluing or hot pressing two plastic foils lying one above the other, the gluing being carried out on all edges of the foils. The interior of the packaging (i.e. the plastic bag) produced by gluing can then be filled with the desired cosmetic preparation. The packaging can be opened by tearing or cutting open the plastic bag.

However, the filling of oxidizing agent preparations into such packaging is associated with problems, the cause of which lies in the reactivity of the oxidizing agent. Oxidizing agents are highly reactive substances which—depending on the storage conditions and possibly on the presence of decomposing impurities—decompose in small proportions with the formation of oxygen (i.e. Gas).

The developer bottles known from the prior art are generally only filled to a maximum of half, usually only a third, of their inner volume with the oxidizing agent composition. As a rule, developer bottles are made of polyethylene. Since polyethylene is permeable to both water vapour and other gases, there is no or only very little excess pressure in the developer bottle. In addition, developer bottles are usually provided with stable, thick walls and a stable screw cap, so that the diffusion of water vapour or gases through the thickness of the walls is reduced and a slight increase in pressure inside the bottle has no negative effects.

In contrast, however, bag-shaped packaging is usually filled completely with the liquid preparation, and there is practically no protruding air space in the filled bag. In addition, such packaging should be flexible, and when opening (e.g. tearing open or cutting open) there should be no uncontrolled leakage of the preparation. For this reason, the formation of excess pressure in the packaging should be avoided as far as possible when packaging liquid preparations.

If an oxidizing agent composition is now in such packaging, the gas (oxygen) formed during storage can cause the packaging to expand. Since the edges of the packaging are usually only glued, excessive inflation will in the worst case cause the packaging to burst. For these reasons, the choice of the film material from which the packaging is made is of great importance when storing compositions containing oxidizing agents.

Packaging made of pure plastic, such as polyethylene or polypropylene, is permeable to both water vapour and gases. The packaging is not inflated when a preparation containing an oxidizing agent is stored in a packaging made of polyethylene or polypropylene. However, due to the high permeability of the comparatively thin film of the packaging to water vapour, the water content of the preparation is reduced. If the preparation is stored in the packaging for a few weeks to months, the water loss exceeds the maximum value permitted for sufficient storage stability.

The production of suitable packaging for formulations containing hydrogen peroxide is a challenge. The properties for the permeability of oxygen and water vapour shown above must be set so that there is sufficient storage stability. The layer thickness of the film should be kept as low as possible for reasons of environmental protection and for the protection of resources. In addition, the layer thickness naturally also has an impact on the manufacturing costs. Against this background, thin layers are desired, but these do not always guarantee sufficient mechanical strength. If different materials are combined in a multilayer film to meet a wide range of requirements, the manufacturability of the multilayer film must also be guaranteed. Certain materials cannot be combined with each other because the cohesion between layers is not always sufficient or because their processing temperatures can be so different that joint processing is difficult.

Finally, the film materials are of great importance especially when storing a multi-component system, since substances from the multi-component system can diffuse into the films and can promote the detachment of layers that form the film. The choice of components of a formulation containing hydrogen peroxide therefore also has an influence on the choice of packaging.

BRIEF SUMMARY

The object of the present application was to pack formulations containing hydrogen peroxide in such a way that the mechanical strength of the packaging is sufficiently large to enable safe storage, but that easy access to the ingredients is ensured.

Surprisingly, it has now been found that oxidizing agent-containing compositions can be packaged in which the water vapour permeability is low and inflation can be reduced by allowing the film a certain degree of oxygen permeability. The films include a special film composite system and also have a barrier layer. By reducing the water vapour permeability, but adjusting the oxygen permeability to a sufficiently high level, the tendency to expand due to oxygen formed from the hydrogen peroxide is reduced and the mechanical strength is increased over time.

The present disclosure relates to a cosmetic product for changing the natural color of keratin fibres, in particular human hair (i) at least one packaging (VP) comprising at least one multilayer film (F) which contains at least a first polymer layer (P1), at least a second polymer layer (P2) and at least one barrier layer (BS), and (ii) at least one cosmetic composition (KM), which is packed in the packaging (VP) and contains:
  a) at least one oxidizing compound,
  b) at least one $C_8$-$C_{30}$-Alcohol,
  c) at least one anionic surfactant, selected from compounds of the formula $R(OCH_2CH_2)_n$—$OSO_3$—$X^+$, where R is saturated or unsaturated $C_8$-$C_{30}$-Alkyl radical, n is an integer from about 10 to about 50 and $X^+$ is a physiologically acceptable cation,
  d) at least one non-ionic surfactant and
  e) at least one thickener selected from the group of copolymers of (meth) acrylic acid and (meth) acrylic acid esters, copolymers of (meth) acrylates and (meth) acrylamides, copolymers of hydroxyethyl (meth) acrylates and (meth) acrylamides, copolymers of (meth) acrylates, (meth) acrylamides and ethoxylated (meth) acrylic esters and mixtures thereof, in particular copolymers of (meth) acrylic acid and acrylic acid ethyl esters, wherein the first polymer layer (P1) is formed from polyethylene terephthalate or polyethylene naphthalate, in particular from polyethylene terephthalate; the second polymer layer (P2) is formed from a polyolefin, in particular polyethylene; and the barrier layer (BS) is formed from a polyester provided with an SiOx layer, in particular from a polyethylene terephthalate provided with an SiOx layer.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Keratinic fibres, keratin containing fibres or keratin fibres are to be understood as furs, wool, feathers and in particular human hair. Although the agents as contemplated herein are primarily suitable for lightening and dyeing keratin fibres, in principle there is nothing to prevent their use in other areas.

The product as contemplated herein is a product for the oxidative colour change of keratin fibres, i.e. a product used on the human head to achieve oxidative coloruring, lightening, bleaching or shading the hair. In this context, shading is understood to mean a colouration in which the colour result is lighter than the original hair colour. That the product is to be used "to change the natural colour" means that the product either comprises only an oxidizing agent for bonding, or that the product comprises an oxidizing agent used with a non-inventive coupler to achieve a colour change, or that the product is used with a non-inventive dye for further tinting.

Furthermore, as contemplated herein, the term "packaging" is understood to mean packaging which is preferably in the form of a sachet. A sachet is a small packaging in the form of a bag or pouch, which is often used in the packaging of cosmetics. The capacity of the packaging, in particular of the sachet, may for example be from about 5 to about 1000 ml, preferably from about 10 to about 200 ml and particularly preferably from about 20 to about 50 ml.

In addition, a multilayer film (F) in the context of the present disclosure is understood to be a thin, flat and windable web including the at least one polymer layer (P1)

and the at least one polymer layer (P2). This multi-layer film (F) forms the wall of the packaging (VP). The packaging also contains a barrier layer (BS), which specifically allows or reduces the passage of water vapour and other gases, such as oxygen.

As contemplated herein, the permeability values of the film (F) are advantageously adjusted. The film (F) thus gives the packaging advantageous barrier properties, in particular with regard to the permeability to water vapour (engl. Water Vapour Transmission Rate; WVTR; measured in in the unit $g/(m^2 d)$ or $g/(m^2\ 24\ h)$) measured according to the ASTM F 1249 method at about 38° C. ambient temperature and about 100% relative atmospheric humidity, and for oxygen (engl.: oxygen transmission rate; OTR, measured in $cm^3/(m^2 d\ bar)$ or $cm^3/(m^2\ 24\ h)$—where $cm^3$ is equivalent to cc—at an atmospheric pressure of about 1 bar) measured according to the ASTM D 3985 method at about 23° C. ambient temperature and about 50% relative air humidity.

Furthermore, the term "non-ionic surfactant" is understood as contemplated herein to mean amphiphilic (bifunctional) compounds which have at least one hydrophobic and at least one hydrophilic part of the molecule. The hydrophobic radical is preferably a hydrocarbon chain with 8 to 28 carbon atoms, which can be saturated or unsaturated, linear or branched. This $C_8$-$C_{28}$-Alkyl chain is particularly preferably linear. In contrast to anionic, cationic, zwitterionic and Amphiphilic surfactants, non-ionic surfactants contain neither cationic nor anionic groups. In addition, these surfactants also have no cationizable and anionizable groups, which can form cationic or anionic groupings depending on the pH.

Finally, in the context of the present disclosure, the term "thickener" is understood to mean compounds which can bind liquids, in particular water, and increase the viscosity of these liquids. In the context of the present disclosure, this also includes gel formers which are able to thicken liquids to form compositions with a gel-like consistency or to form gels. As contemplated herein, gel-like cosmetic agents or gels are dimensionally stable, easily deformable disperse systems composed of at least two components, the gel former (usually a solid, colloid-divided substance with long or strongly branched compounds) and a liquid (usually water) as a dispersant. The gel former forms a spatial network in the liquid, whereby the individual gel-forming compounds adhere to each other at different spatial points through major and/or minor valences. In this context, the term (meth)acrylate includes both methacrylates and acrylates. Suitable thickeners are, for example, those available under the following INCI designations: acrylates copolymer, sodium acrylate/sodium acryloyldimethyl taurate copolymer, hydroxyethyl acrylate sodium acryloyldimethyl taurate copolymer, polyacrylates crosspolymer 6, ammonium acryloyl dimethyl taurate ($NH_4AMPS$), dimethyl acrylamide, lauryl methacrylate and laureth-4 methacrylate.

The cosmetic product as contemplated herein comprises as first component a packaging (VP) comprising at least one multilayer film (F). This film contains at least one first polymer layer (P1), at least one second polymer layer (P2) and at least one barrier layer (BS). This multi-layer film represents the wall or outer cover of the packaging. As described above, such packaging is usually produced by gluing, pressing or welding two pieces of film on top of each other (the packaging (VP) is filled at the same time as the cosmetic composition (KM) i.e. such packaging is closed at all edges. This packaging can be opened, for example, by tearing or cutting open.

The thickness of the multilayer film (F) determines the mechanical properties and strength of the films. It should be designed in such a way that there is sufficient mechanical stability, but at the same time the film (F)—and thus the packaging (VP) produced from the film—should be flexible enough to allow complete removal of the cosmetic composition (KM) from the opened packaging (VP) by compression or squeezing. A film meets these requirements if the film (F) has a certain total thickness. Preferred embodiments of the present disclosure at least one multilayer film has a total thickness of from about 28 μm to about 220 μm, preferably from about 52 μm to about 180 μm, further preferably from about 80 μm to about 140 μm. For the purposes of the present disclosure, the total thickness of the film (F) is understood to be the sum of the thicknesses of all individual layers of which the film (F) is made.

The arrangement of the layers (P1), (P2) and (BS) within the multilayer film (F) can be different. Furthermore, it is also possible for the film (F) to comprise further layers in addition to the layers mentioned above. In addition, it is advantageous as contemplated herein if all the layers mentioned above are each oriented parallel to the surfaces of the film (F), that is to say all the layers have the same orientation. If the multilayer film (F) contains the three layers (P1), (P2) and (BS) described above, the following arrangements of the layers would be possible (from the inside (considered in contact with the cosmetic composition (KM)) to the outside):
a) *Interior*-Layer (P1)-Layer (P2)-Barrier layer (BS)-*Exterior*,
b) *Interior*-Layer (P1)-Barrier layer (BS)-Layer (P2)-*Exterior*,
c) *Interior*-Layer (P2)-Layer (P1)-Barrier layer (BS)-*Exterior*,
d) *Interior*-Layer (P2)-Barrier layer (BS)-Layer (P1)-*Exterior*,
e) *Interior*-Barrier layer (BS)-Layer (P1)-Layer (P2)-*Exterior*,
f) *Interior*-Barrier layer (BS)-Layer (P2)-Layer (P1)-*Exterior*.

However, as contemplated herein, it is preferred when the barrier layer (BS) is located between the first polymer layer (P1) and the second polymer layer (P2), the second polymer layer (P2) being located on the outside of the package. In this case, the multilayer film (F) includes three layers, the layer (P1) being the innermost and in contact with the cosmetic composition (KM). The layer (P1) is in contact with the barrier layer (BS), and the barrier layer (BS) is in contact with the layer (P2). In this layer the layers (P1) and (P2) are not adjacent to each other, but are separated by the barrier layer (BS). The particular advantage of this arrangement is that the—often very thin—barrier layer (BS) is located neither on the inner nor on the outer surface of the multilayer film (F), but is protected towards the inside by the polymer layer (P1) and towards the outside by the polymer layer (P2). In this way, mechanical abrasion or mechanical destruction of the barrier layer (BS) can be avoided as far as possible. It is therefore advantageous in the context of the present disclosure if the at least one multilayer film (F) contains the at least one barrier layer (BS) between the at least one first polymer layer (P1) and the at least one second polymer layer (P2). The use of such packaging has proven to be particularly advantageous in terms of increased storage stability, as this arrangement shows neither swelling nor delamination on prolonged contact with a composition containing an oxidant. In a further preferred embodiment, the barrier layer (BS) is also arranged between the two polymer layers P1 and P2, but the first polymer layer (P1) is located on the outside of the packaging.

As contemplated herein, the outside of the packaging (VP) is the side of the packaging which does not come into contact with the cosmetic composition (KM) but with the environment. The use of such packaging has proven to be particularly advantageous in terms of increased storage stability, as this arrangement shows neither swelling nor delamination on prolonged contact with a composition containing an oxidant.

The first polymeric material of the first layer (P1) is a polyester. This material can be a layer of one polymer type or a layer of a polymer mixture. According to the present disclosure, at least one first polymer layer (P1) is formed from polyethylene terephthalate or polyethylene naphthalate, in particular polyethylene terephthalate. As contemplated herein, the term "formed" is understood to mean that the polymer layer contains at least about 70% by weight, preferably at least about 80% by weight, preferably at least about 90% by weight, in particular at least about 99% by weight, each based on the total weight of the polymer layer (P1), of the above-mentioned compounds.

Polyethylene terephthalate (PET) is a polymer from the polyester group. Polyethylene terephthalate can be produced, for example, by transesterification of dimethyl terephthalate with ethylene glycol at higher temperatures. In this transesterification reaction, methanol is split off, which is removed by distillation. The resulting bis(2-hydroxyethyl) terephthalate is converted to PET by polycondensation, which again producing ethylene glycol. Another method of producing polyethylene terephthalate is the direct polycondensation of ethylene glycol and terephthalic acid at high temperatures while distilling off the water formed. Polyethylene terephthalate is exemplified by a particularly high mechanical strength. If the PET layer forms the outer layer, this also has the advantage that the layer can be printed underneath without the print being rubbed off. The PET layer is transparent and offers a mechanical protective layer for the print layer.

According to a preferred embodiment of the present disclosure, the layer thickness of the first polymer layer (P1) is from about 4 µm to about 50 µm, preferably from about 5 µm to about 35 µm, more preferably from about 6 µm to about 20 µm. The layer thickness of the PET layer used according to the preferred embodiment is associated with particular advantages, which is related to general properties of PET. PET is exemplified by high dimensional stability/rigidity. If PET with these layer thicknesses is selected as the first polymer layer (P1), this offers an advantageous mechanical dimensional stability for the film. At the same time, the total thickness of the film can be kept low so that a film that conserves material and resources can be provided.

Furthermore, the multilayer film (F) from which the packaging is produced comprises a second polymer layer (P2) made of a second polymeric material. The second polymeric material can be a layer of a polymer type or a layer of a polymer mixture. It is provided in the context of the present disclosure that the at least one second polymer layer (P2) is formed from a polyolefin, in particular from polyethylene. As contemplated herein, the term "formed" is understood to mean that the polymer layer contains at least about 70% by weight, preferably at least about 80% by weight, preferably at least about 90% by weight, in particular at least about 99% by weight, each based on the total weight of the polymer layer (P2), of the above-mentioned compounds.

As contemplated herein, the second polymeric material of the second layer (P2) of the multilayer film (F) is a polyolefin, in particular polyethylene. Polyolefins are polymers, that are produced from alkenes such as ethylene, propylene, 1-butene or isobutene by chain polymerization. The polyolefins are saturated hydrocarbons. They are semi-crystalline Thermoplastics, that are easy to process. They are exemplified by good chemical resistance. Polyethylene and polypropylene are very widespread in film applications. As contemplated herein, polypropylene, but more preferably polyethylene, is therefore used for the second layer (P2). Polyethylene is made by polymerizing ethylene using various catalysts. For example, polyethylene can be produced by polymerizing ethylene in the gas phase or in suspension. The average relative molar mass can be regulated, for example, by setting a certain hydrogen partial pressure during the polymerization of ethylene. Polyethylene can be processed, for example, by extrusion and stretch blow moulding, or by pressing, calendering, thermoforming and cold forming.

The second polymer layer (P2) serves as a support layer. Although polyethylene has the disadvantage of being permeable to oxygen and water vapour, it has the advantage of being inexpensive and, due to its low melting point—lower than that of polypropylene—it is easy and energy-saving to process.

According to a preferred embodiment of the present disclosure, the second polymer layer (P2) has a certain layer thickness. According to the preferred embodiment, the second polymer layer (P2) has a layer thickness of from about 20 µm to about 150 µm, preferably from about 30 µm to about 110 µm, highly preferable from about 40 µm to about 90 µm. In particular, the second polymer layer (P2) has a higher layer thickness than the first polymer layer (P1).

The polymer layers (P1) and (P2) of the multilayer film (F) comprise organic polymeric materials, which usually have only an insufficient barrier effect against gases and water vapour. If the oxidant-containing composition (KM) is packaged in a package (VP) made of a multilayer film (F) which comprises only the two organic polymer layers (P1) and (P2), water vapour can escape unhindered, so that the water content in the composition (KM) changes in an unacceptable manner during prolonged storage. To specifically minimize the uncontrolled escape of water vapour from the packaging (VP), the organic polymer layers (P1) and (P2) are therefore used in combination with a barrier layer (BS).

The barrier layer (BS) has a penetration barrier effect for gases and water vapour. As contemplated herein, this means that the barrier layer (BS) reduces and controls the permeation rate of water vapour and gases through the film. A film (F) as contemplated herein, which has a barrier layer (BS) in addition to the layers (P1) and (P2), thus has a reduced water vapour permeability and a reduced gas permeability compared to a comparable film (with the same overall thickness), which has only the two layers (P1) and (P2), but no barrier layer (BS).

The barrier layer (BS), for example, is a thin layer comprising an inorganic material, whereby the inorganic material can be applied to organic polymer layers using vacuum coating techniques (e.g. PVD "physical vapour deposition" or CVD "chemical vapour deposition").

If the barrier layer (BS) is a layer comprising at least one inorganic material, metals, semi metals or metal or semi metallic oxides, for example aluminium, aluminium oxides, magnesium, magnesium oxides, silicon, silicon oxides, titanium, titanium oxides, tin, tin oxides, zirconium, zirconium oxide and/or carbon may be used for films.

As contemplated herein, the barrier layer (BS) is formed from a polyester provided with an $SiO_x$ layer, in particular from a polyethylene terephthalate provided with an $SiO_x$ layer. The $SiO_x$ layer is particularly well compatible with the adjacent polyethylene layer.

According to a particularly preferred embodiment of the present disclosure, the polyethylene terephthalate layer of the barrier layer (BS) is part of the first layer (P1). In other words, the $SiO_x$ is deposited on the first layer (P1). The layer thickness of the PET layer then corresponds to the layer thickness of the PET layer that is part of the barrier layer (BS) and the layer thickness that is part of the first layer (P1).

The polyethylene terephthalate film is provided with a $SiO_x$ layer. The silicon oxide is evaporated onto the polyethylene terephthalate film and is primarily responsible for the barrier effect. The ratio of the thickness of $SiO_x$ to polyethylene terephthalate in a preferred embodiment of the present disclosure is from about 1:1000 to about 1:10, preferably from about 1:500 to about 1:50, more preferred from about 1:200 to about 1:100.

The production of films with barrier layers comprising inorganic material is well known. The multilayer film (F) used as contemplated herein can also be produced by a process which is used for the production of known films with barrier layers in the state of the art, as described in the documents EP 1036813 A1, EP 2371539 A1 and EP 1541340 A1.

The barrier layer (BS) can additionally also comprise a thin layer of inorganic-organic hybrid polymers. These polymers are known in the literature under the technical term ORMOCER polymers. A typical ORMOCER polymer can be produced, for example, by hydrolytic polycondensation of an organo-functional silane with an aluminium compound and optionally with an inorganic oxide component. Corresponding syntheses are revealed, for example, in the paper EP 0792846 B1, to which full reference is made at this point. Inorganic-organic hybrid polymers (ORMOCER polymers) have both inorganic and organic network structures. The inorganic silicate network structure can be built up in the sol-gel process via the controlled hydrolysis and condensation of alkoxysilanes. By including additional metal alkoxides in the sol-gel process, the silicate network can be specifically modified. By polymerization of organo-functional groups, which are introduced into the material by the organoalkoxylanes, an additional organic network is built up. The ORMOCER polymers produced in this way can be applied to layers (P1) and/or (P2) using conventional application techniques (spraying, brushing, etc.).

The thicker the barrier layer (BS), the greater or stronger is the penetration barrier effect for gases and water vapour. The thickness of the barrier layer (BS) can therefore be selected depending on the desired barrier layer effect. According to a preferred embodiment of the present disclosure, the at least one barrier layer (BS) has a layer thickness of from about 4 μm to about 20 μm, preferably of from about 5 μm to about 18 μm, more preferably of from about 6 μm to about 15 μm.

The material, structure and layer thicknesses determine the permeability values of the film. The multilayer film (F) of the packaging of the cosmetic product subject to the present disclosure is exemplified by advantageous properties with respect to oxygen permeability and water vapor permeability. The multilayer film exhibits an oxygen transmission rate (OTR) at about 23° C. and about 50% relative humidity of from about 0.1 to about 5 $cc/m^2/d/bar$, preferably from about 0.2 to about 3.5 $cc/m^2/d/bar$, more preferably from about 0.5 to about 2.5 $cc/m^2/d/bar$, and a water vapour transmission rate at about 38° C. and about 100% relative humidity of from about 0.1 to about 5 $g/m^2d$, preferably from about 0.2 to about 3.5 $g/m^2d$, more preferably from about 0.5 to about 2.5 $g/m^2d$.

As contemplated herein, the permeability values of the film (F) are advantageously adjusted. The film (F) thus gives the packaging advantageous barrier properties, in particular with regard to the permeability to water vapour (engl. water vapor transmission rate; WVTR; measured in in the unit $g/(m^2d)$ or $g/(m^2\ 24\ h)$) measured according to the ASTM F 1249 method at about 38° C. ambient temperature and about 100% relative atmospheric humidity, and for oxygen (engl.: oxygen transmission rate; OTR, measured in $cm^3/(m^2d\ bar)$ or $cm^3/(m^2\ 24\ h)$—where $cm^3$ is equivalent to cc—at an atmospheric pressure of about 1 bar) measured according to the ASTM D 3985 method at about 23° C. ambient temperature and about 50% relative air humidity.

In addition to the layers (P1), (P2) and (BS) described so far, the multilayer film (F) can also include one or more additional layers. These additional layers can for example be intermediate layers and/or adhesive layers. As contemplated herein, it is therefore preferred if at least one multilayer film (F) additionally contains at least one further layer selected from the group of intermediate layers (SZ), adhesive layers (SK) and mixtures thereof.

For example, the foils (F) can have further intermediate layers (SZ) to increase the mechanical stability. Interlayers can also prevent or minimize the permeation of polymers or remaining monomers from a polymer layer into the cosmetic composition (KM).

To increase bond strength, the films can also include one or more adhesive layers (SK) to reduce or prevent delamination (i.e. peeling or the formation of an air space) between two layers.

A particularly preferred product as contemplated herein multilayer film (F) contains, in addition to the first polymer layer (P1), the second polymer layer (P2) and the barrier layer (BS), one or more further layers selected from intermediate layers (SZ) and/or adhesive layers (SK).

If the multilayer film (F) contains layers (P1), (P2) and (BS) in addition to the layers (P1), (P2) and (BS), the following arrangements of the layers are possible (from interior (in contact with the cosmetic composition (KM)) to exterior):

a) *Interior*-Layer (P1)-First adhesive layer (SK1)-Layer (P2)-Second adhesive layer (SK2)-Barrier Layer (BS)-*Exterior*,
b) *Interior*-Layer (P1)-Adhesive Layer (SK1)-Layer (P2)-Barrier Layer (BS)-*Exterior*,
c) *Interior*-Layer (P1)-Layer (P2)-Second adhesive layer (SK2)-Barrier layer (BS)-*Exterior*,
d) *Interior*-Barrier layer (BS)-First adhesive layer (SK1)-Layer (P1)-Second adhesive layer (SK2)-Layer (P2)-*Exterior*,
e) *Interior*-Barrier layer (BS)-Adhesive Layer (SK)-Layer (P1)-Layer (P2)-*Exterior*,
f) *Interior*-Barrier layer (BS)-Layer (S1)-Adhesive Layer (SK)-Layer (P2)-*Exterior*,
g) *Interior*-Layer (P1)-First adhesive layer (SK1)-Barrier layer (BS)-Second adhesive layer (SK2)-Layer (P2)-*Exterior*,
h) *Interior*-Layer (P1)-Adhesive Layer (SK)-Barrier layer (BS)-Layer (P2)-*Exterior*,
i) *Interior*-Layer (P1)-Barrier layer (BS)-Adhesive Layer (SK)-Layer (P2)-*Exterior*

In any case, the film should be designed so that there is sufficient adhesion between the films. According to a preferred embodiment of the present disclosure, the bond strength (engl.: bond strength) of the film from about 0.1 to about 10 N/15 mm, preferably from about 1 to about 8 N/15 mm, more preferably from about 1.5 to about 5 N/15 mm This is measured by the ASTM F-904 method. Adhesive strength is a physical measure of the adhesive force between the layers. The adhesive strength is related to the two layers of a film with the lowest adhesive strength between two layers of the same film. The adhesive strengths adjusted as contemplated herein lead to a favourable mechanical stability over the storage time of the packaged cosmetic product.

The strength between two bonded (sealed or unsealed) films should also be sufficient. According to a preferred embodiment of the present disclosure, the seal strength (engl.: seal strength) of the packaging (VP) is from about 10 to about 40 N/15 mm, preferably from about 15 to about 35 N/15 mm, more preferably from about 20 to about 30 N/15 mm, under the conditions of about 150° C., about 2.54 cm (about 1") and about 4 kg/cm$^2$. The seal seam strength is measured according to the ASTM F-88 method under the conditions mentioned. The challenge with packaging is always to ensure the mechanical durability of the packaging with easy access to the contents by the user. Setting the seal strength to these values makes it possible to achieve these two goals.

A sealed seam is a seam by which the packaging is closed. Usually, two films are placed on top of each other for closing the package and are pressed together by a force perpendicular to the film surface. By heating the films in the area that is compressed, parts of the compressed areas can fuse together so that the films are welded together. There may also be an adhesive between the compressed foils, which strengthens the seam.

The product as contemplated herein comprises as a second ingredient a cosmetic composition (KM) packaged in the packaging (VP) and containing at least one oxidizing agent, at least one $C_8$-$C_{30}$-Alcohol, at least one specific anionic surfactant, at least one non-ionic surfactant and at least one acrylic acid polymer as thickening agent.

The intended use of the product as contemplated herein is oxidative colour change. For this purpose, as described above, a cosmetic composition (KM) containing an oxidizing agent is usually mixed with a second preparation (B) separately prepared from (KM). In this way the ready-to-use oxidative colour changing agent is produced. Depending on whether the oxidative colour change is intended to bleach, lighten or colour, the preparation (B) may contain different ingredients. If pure lightening or bleaching is to be achieved, the preparation (B) contains at least one alkalising agent. If oxidative dyeing is desired, preparation (B) often contains oxidation dye precursors in addition to the alkalising agent. In order to ensure that the preparations (KM) and (B) can be mixed sufficiently quickly, both the preparation (KM) and the preparation (B) are usually flowable, aqueous or water-containing preparations.

As contemplated herein, the preparation (KM) is an aqueous preparation. The water content of the preparation (KM) may be—based on the total weight of the preparation (KM)—for example from about 60 to about 97% by weight, preferably from about 75 to about 93% by weight, preferably from about 78 to about 91% by weight, in particular from about 80 to about 88.0% by weight. All weight indications in % by weight refer to the total weight of water contained in the preparation (KM) in relation to the total weight of the preparation (KM).

The cosmetic composition (KM) as a first essential ingredient, a) at least one oxidizing agent. Certain oxidizing agents are preferred over others. It is therefore advantageous in the context of the present disclosure if the cosmetic composition (KM) contains at least one oxidising compound selected from the group including persulphates, chlorites, hydrogen peroxide and products of the addition of hydrogen peroxide to urea, melamine and sodium borate, in particular hydrogen peroxide. The use of hydrogen peroxide has proven to be particularly advantageous.

The concentration of the oxidizing agent in the composition (KM) is determined on the one hand by the legal requirements and on the other hand by the desired effect; preferably from about 0.5 to about 20.0% by weight solutions in water are used. It is therefore preferred, as contemplated herein, when the cosmetic composition (KM) contains the at least one oxidizing compound, in particular hydrogen peroxide, in a total amount of from about 0.5 to about 20% by weight, preferably from about 1.0 to about 18% by weight, preferably from about 1.2 to about 16% by weight, in particular from about 1.5 to about 15% by weight, based on the total weight of the cosmetic composition (KM). The higher the content of oxidant, especially hydrogen peroxide, in the composition (KM), the greater is the amount of gas produced by a proportional decomposition of the oxidant. Preparations containing higher concentrations of oxidizing agents are therefore much more difficult to store in a packaging (VP) than less concentrated preparations. The amount of hydrogen peroxide here refers to 100% hydrogen peroxide.

In the course of the work leading to this present disclosure, it turned out that the product as contemplated herein is particularly suitable for the packaging and stable storage of higher concentrated hydrogen peroxide preparations (KM). For example, packaging (VP) as contemplated herein containing preparations (KM) with from about 9 to about 12 wt. % hydrogen peroxide showed no volume changes (i.e. no swelling) and no unplanned openings (i.e. the packaging did not burst open) even after storage at elevated temperature for several weeks.

The cosmetic composition (KM) contains at least one $C_8$-$C_{30}$-Alcohol as the second essential ingredient b). In this context, mixtures of linear $C_{14}$-$C_{18}$-Alcohols have proved particularly successful. Such mixtures, in combination with the other features c) to e) of the composition (KM), result in excellent stabilization of the at least one oxidizing agent, in particular hydrogen peroxide. It is therefore advantageous in the context of the present disclosure if the cosmetic composition (KM) contains at least one $C_{10}$-$C_{30}$-alcohol alcohol selected from the group of linear $C_{10}$-$C_{28}$-alcohols, linear $C_{12}$-$C_{26}$-alcohols, linear $C_{14}$-$C_{20}$-alcohols, linear $C_{14}$-$C_{18}$-alcohols and mixtures of the aforementioned alcohols, in particular a linear $C_{14}$-$C_{18}$-alcohol or a mixture of linear $C_{14}$-$C_{18}$-alcohols. In the context of the present disclosure, the mixture of cetyl alcohol and stearyl alcohol known as cetearyl alcohol, in particular a mixture of 50% by weight of cetyl alcohol and 50% by weight of stearyl alcohol, based on the total weight of the mixture, has proved to be particularly advantageous. Furthermore, the use of a linear $C_{14}$-$C_{18}$-alcohol, especially cetyl alcohol, has proven to be particularly advantageous.

The at least one $C_8$-$C_{30}$-alcohol is preferably used in certain quantity ranges. Preferred embodiments of the present disclosure cosmetic composition (KM) comprises the at least one $C_8$-$C_{30}$-alcohol, in particular a linear $C_{14}$-$C_{18}$-alcohol or a mixture of linear $C_{14}$-$C_{18}$-alcohols, in a total amount of from about 0.10 to about 7.0 wt.-%, preferably from about 0.50 to about 6.5% by weight, preferably from about 1.0 to about 6.0% by weight, in particular from about 1.5 to about 5.0% by weight, based on the total weight of the cosmetic composition (KM). The use of the above-mentioned total quantities of the at least one $C_8$-$C_{30}$-alcohol, in particular a linear $C_{14}$-$C_{18}$-alcohol or the mixture of linear $C_{14}$-$C_{18}$-alcohols, in combination with the other ingredients of the cosmetic composition (KM) leads to a particularly good stabilization of the oxidizing agent contained in this composition, in particular hydrogen peroxide.

As third essential ingredient (c), the cosmetic composition (KM) contains at least one specific anionic surfactant. The use of these surfactants ensures sufficient miscibility of the cosmetic composition (KM) with the preparation (B) containing the oxidation dye precursors and also ensures a high storage stability by preventing precipitation of components of the cosmetic composition (KM). Preferred embodiments of the present disclosure cosmetic composition (KM) contains at least one anionic surfactant chosen from compounds of formula $R(OCH_2CH_2)_n$—$OSO_3$—$X_+$, in which R represents saturated or unsaturated $C_{12}$-$C_{20}$-alkyl radicals, n represents integers from about 25 to about 35 and $X^+$ represents sodium. An anionic surfactant particularly suitable in the context of the present disclosure is the compound known under the INCI designation sodium coceth-30 sulfate (CAS No.: 68891-38-3).

To ensure a sufficient dispersion of all ingredients of the cosmetic product (KM), the at least one anionic surfactant is preferably used in certain total amounts. It is therefore preferred in the context of the present disclosure if the cosmetic composition (KM) contains the at least one anionic surfactant, in particular compounds of the formula $R(OCH_2CH_2)_n$—$OSO_3$—$X_+$, where R is saturated or unsaturated $C_{12}$-$C_{20}$-alkyl radicals, n is an integer from about 25 to about 35 and $X^+$ represents sodium, in a total amount of from about 0.10 to about 7.0% by weight, preferably from about 0.10 to about 5.0% by weight preferably from about 0.15 to about 4.0% by weight, in particular from about 0.20 to about 3.5% by weight, by weight relative to the total weight of the cosmetic composition (KM).

The fourth essential component d) contains the cosmetic composition (KM) at least one non-ionic surfactant. The combination of anionic and non-ionic surfactant results in excellent dispersion of the components of the cosmetic composition (KM) and thus high storage stability. In addition, the use of such surfactant combinations leads to a good spreadability, especially miscibility, of the cosmetic composition (KM) with the preparation (B) containing the oxidation dye precursors. It is therefore preferred in the context of the present disclosure if the cosmetic composition (KM) contains at least one non-ionic surfactant selected from the group of (i) ethoxylated and/or propoxylated alcohols and carboxylic acids having 8 to 30 carbon atoms and 2 to 30 ethylene oxide and/or propylene oxide units per mole of alcohol, (ii) addition products of 30 to 50 moles of ethylene oxide to castor oil and hydrogenated castor oil, (iii) alkyl polyglucosides corresponding to the formula $R^1O$-$[G]_p$, in which $R^1$ is an alkyl and/or alkenyl radical containing 4 to 22 carbon atoms, G is a sugar unit containing 5 or 6 carbon atoms and p is a number of 1 to 10, (iv) monoethanolamine of carboxylic acids containing 8 to 30 carbon atoms and (v) mixtures thereof, more particularly ethoxylated alcohols containing 14 to 18 carbon atoms and 20 to 30 ethylene oxide units per mole of alcohol. In the formula $R^1O$-$[G]_p$, the index number p indicates the degree of oligomerisation (DP), i.e. the distribution of monoglucosides and oligoglucosides, and is a number between 1 and 10. While p in a given compound must always be an integer and, in particular, can assume the values p=1 to 6, the value p for a particular alkyl oligoglucoside is an analytically determined arithmetical quantity which usually represents a fractional number. As contemplated herein, alkyl and/or alkenyl oligoglucosides with an average degree of oligomerisation p of from about 1.1 to about 3.0 are preferably used. From an application technology point of view, those alkyl and/or alkenyl oligoglucosides are preferred whose degree of oligomerisation is less than about 1.7 and in particular lies between about 1.2 and about 1.7. The alkyl or alkenyl radical $R^1$ can be derived from primary alcohols containing 4 to 20, preferably 8 to 16 carbon atoms. As contemplated herein, alkyl oligoglucosides based on hardened $C_{12/14}$-Coconut alcohol with a DP of 1-3, such as those commercially available under the INCI designation "coco-glucosides", are particularly preferred. The non-ionic surfactants particularly preferred in the context of the present disclosure are ethoxylated alcohols with 14 to 18 carbon atoms and 20 to 30 moles of ethylene oxide units per mole of alcohol, in particular the compound known under the INCI designation ceteareth-20 (CAS-No.: 68439-49-6).

According to a particularly preferred embodiment of the present disclosure, the anionic surfactant c) of the cosmetic composition (KM) is a sodium sulphate of a linear $C_{12}$-$C_{14}$-Alkyl ethoxylate with 30 ethylene oxide units per surfactant molecule, for example the commercially available product Disponil® FES 77, and/or is the non-ionic surfactant d) of the cosmetic composition (KM) a linear $C_{16}$-$C_{18}$ ethoxylated alcohol with 20 ethylene oxide units per surfactant molecule, for example the commercially available product ceteareth-20. In this particularly preferred embodiment of the present disclosure, it is particularly preferred that the sodium sulfate of a linear $C_{12}$-$C_{14}$-alkyl ethoxylate containing 30 ethylene oxide units per surfactant molecule is present in an amount of 1 to 3.0% by weight, based on the total weight of the cosmetic composition (KM), is contained in the cosmetic composition (KM), and/or the linear $C_{16}$-$C_{18}$ ethoxylated alcohol with 20 ethylene oxide units per surfactant molecule is contained in the cosmetic composition (KM) in an amount of from about 0.5 to about 2.0% by weight, based on the total weight of the cosmetic composition (KM). This combination of features has proven to be particularly advantageous for solving the problem underlying the present disclosure.

To ensure a sufficient dispersion of all ingredients of the cosmetic product (KM), the at least one non-ionic surfactant is preferably used in certain total amounts. Preferred embodiments of the present disclosure cosmetic composition (KM) contains at least one non-ionic surfactant, in particular ethoxylated alcohols and having 14 to 18 carbon atoms and 20 to 30 ethylene oxide units per mole of alcohol, in a total amount of from about 0.10 to about 4.0% by weight of the total amount of the present disclosure. %, preferably from about 0.15 to about 3.8% by weight, preferably from about 0.20 to about 3.5% by weight, in particular from about 0.30 to about 2.0% by weight, by weight relative to the total weight of the cosmetic composition (KM).

As fifth essential ingredient (e), the cosmetic composition (KM) contains at least one specific thickener. In this context, copolymers of (meth)acrylic acid and acrylic acid ethyl ester have proven to be particularly advantageous because these copolymers ensure sufficient thickening over a long period of time, even under strongly acidic conditions and in the presence of an oxidizing agent. The thickening ensures a good handling of the cosmetic composition (KM). To ensure sufficient thickening, at least one thickening agent is preferably used in certain quantity ranges. It is therefore advantageous in the context of the present disclosure if the cosmetic composition (KM) contains the at least one thickener, in particular copolymers of (meth)acrylic acid and acrylic acid ethyl ester, in a total amount of from about 0.20 to about 6.0% by weight, preferably of from about 0.25 to about 5.5% by weight, preferably of from about 0.30 to about 5.0% by weight, in particular of from about 0.40 to about 4.5% by weight, based on the total weight of the cosmetic composition (KM). The use of copolymers of (meth)acrylic acid and acrylic acid ethyl ester, which are commercially available under the trade name aculyn 33 A, has proved particularly successful in the context of the present disclosure.

In the course of the work leading to this present disclosure, it was found that the use of the aforementioned essential ingredients b) to e) ensures that the cosmetic composition (KM) containing at least one oxidizing agent can be packaged and stored in the special packaging (VP) without this packaging—which has a barrier layer with a passage barrier effect for gases and water vapour—swelling or bursting.

In this context, a very specific combination of the essential ingredients a) to e) of the cosmetic composition (KM) has proven to be advantageous. In a preferred embodiment, the product as contemplated herein cosmetic composition (KM) comprises hydrogen peroxide, a mixture of linear $C_{14}$-$C_{18}$-Alcohols, an anionic surfactant selected from compounds of formula $R(OCH_2CH_2)_n$—$OSO_3$—$X_+$, where R is saturated or unsaturated $C_{12}$-$C_{20}$-Alkyl radical, n is an integer from about 25 to about 35 and X+ is sodium, an ethoxylated alcohol having 14 to 18 carbon atoms and 20 to 30 ethylene oxide units per mole of alcohol, and a copolymer of (meth)acrylic acid and acrylic acid ester.

For further optimization of storage stability, the above mentioned compounds are preferably used in certain quantity ranges in the preparation (KM). Particularly preferred designs that the cosmetic composition (KM) contains a) from about 1.5 to about 15% by weight of hydrogen peroxide,
b) from about 1.5 to about 5.0% by weight of a mixture of linear $C_{14}$-$C_{18}$ alcohols,
c) from about 0.20 to about 3.5% by weight of an anionic surfactant selected from compounds of formula $R(OCH_2CH_2)_n$—$OSO_3$—$X_+$, wherein R represents saturated or unsaturated $C_{12}$-$C_{20}$-alkyl radicals, n represents integers from 25 to 35 and $X^+$ represents sodium,
d) from about 0.30 to about 2.0% by weight of an ethoxylated alcohol having 14 to 18 carbon atoms and 20 to 30 ethylene oxide units per mole of alcohol, and
e) from about 0.40 to about 4.5% by weight of a copolymer of (meth)acrylic acid and acrylic acid ethyl ester.

The cosmetic composition (KM) preferably has an acidic pH in order to avoid or reduce decomposition of the oxidizing agent used, in particular hydrogen peroxide. It is therefore preferred in the context of the present disclosure that the cosmetic composition (KM) has a pH value (measured at about 20° C.) of from about pH 1.5 to about pH 5.0, preferably of from about pH 2.0 to about pH 4.7, preferably of from about pH 2.3 to about pH 4.4, in particular of from about pH 2.5 to about pH 4.

The preparation (KM) in the packaging (VP) contains the essential ingredients in an aqueous or aqueous-alcoholic carrier, which can be a cream, an emulsion, a gel or even a surfactant-containing foaming solution. To achieve the desired properties of these dosage forms, the preparation (CM) may still contain additional active substances, auxiliaries and additives.

For example, the preparation (KM) may additionally contain one or more acids to stabilise the oxidising agent used, in particular hydrogen peroxide. It is therefore preferred in the context of the present disclosure if the cosmetic composition (KM) additionally contains at least one acid selected from the group of dipicolinic acid, citric acid, acetic acid, malic acid, lactic acid, tartaric acid, hydrochloric acid, phosphoric acid, pyrophosphoric acid and their salts, benzoic acid and salts thereof, 1-hydroxyethane-1,1-diphosphonic acid, ethylenediaminetetraacetic acid and salts thereof, sulphuric acid and mixtures, in particular a mixture of dipicolinic acid, disodium pyrophosphate, benzoic acid and salts thereof and 1-hydroxyethane-1,1-diphosphonic acid.

A particularly high stabilization of the oxidizing agent, especially hydrogen peroxide, is achieved when the abovementioned acids are used in certain quantity ranges. It is therefore advantageous in this context if the at least one acid, in particular the mixture of dipicolinic acid, disodium pyrophosphate and 1-hydroxyethane-1,1-diphosphonic acid, is present in a total amount of from about 0.1 to about 3.0% by weight, preferably of from about 0.5 to about 2.5% by weight, preferably of from about 0.8 to about 2.0% by weight, in particular of from about 0.9 to about 1.5% by weight, relative to the total weight of the cosmetic composition (KM).

The following tables list particularly preferred forms AF 1 to AF 32 of the cosmetic composition (KM) contained in the packaging (VP) (all figures in % by weight unless otherwise stated).

|  | AF 1 | AF 2 | AF 3 | AF 4 |
| --- | --- | --- | --- | --- |
| Oxidising agent | 0.5-20 | 1.0-18 | 1.2-16 | 1.5-15 |
| $C_8$-$C_{30}$-alcohol | 0.10-7.0 | 0.50-6.5 | 1.0-6.0 | 1.5-5.0 |
| Anionic surfactant [2] | 0.10-7.0 | 0.10-5.0 | 0.15-4.0 | 0.20-3.5 |
| Non-ionic surfactant | 0.10-4.0 | 0.15-3.8 | 0.20-3.5 | 0.30-2.0 |
| Thickening agent [3] | 0.20-6.0 | 0.25-5.5 | 0.30-5.0 | 0.40-4.5 |
| Cosmetic carrier [1] | ad 100 | ad 100 | ad 100 | ad 100 |

|  | AF 5 | AF 6 | AF 7 | AF 8 |
| --- | --- | --- | --- | --- |
| Oxidizing agent [4] | 0.5-20 | 1.0-18 | 1.2-16 | 1.5-15 |
| $C_8$-$C_{30}$-alcohol | 0.10-7.0 | 0.50-6.5 | 1.0-6.0 | 1.5-5.0 |
| Anionic surfactant [2] | 0.10-7.0 | 0.10-5.0 | 0.15-4.0 | 0.20-3.5 |
| Non-ionic surfactant | 0.10-4.0 | 0.15-3.8 | 0.20-3.5 | 0.30-2.0 |
| Thickening agent [3] | 0.20-6.0 | 0.25-5.5 | 0.30-5.0 | 0.40-4.5 |
| Cosmetic carrier [1] | ad 100 | ad 100 | ad 100 | ad 100 |

|  | AF 9 | AF 10 | AF 11 | AF 12 |
| --- | --- | --- | --- | --- |
| Oxidizing agent [4] | 0.5-20 | 1.0-18 | 1.2-16 | 1.5-15 |
| $C_8$-$C_{30}$-alcohol [5] | 0.10-7.0 | 0.50-6.5 | 1.0-6.0 | 1.5-5.0 |
| Anionic surfactant [2] | 0.10-7.0 | 0.10-5.0 | 0.15-4.0 | 0.20-3.5 |
| Non-ionic surfactant | 0.10-4.0 | 0.15-3.8 | 0.20-3.5 | 0.30-2.0 |
| Thickening agent [3] | 0.20-6.0 | 0.25-5.5 | 0.30-5.0 | 0.40-4.5 |
| Cosmetic carrier [1] | ad 100 | ad 100 | ad 100 | ad 100 |

|  | AF 13 | AF 14 | AF 15 | AF 16 |
| --- | --- | --- | --- | --- |
| Oxidizing agent [4] | 0.5-20 | 1.0-18 | 1.2-16 | 1.5-15 |
| $C_8$-$C_{30}$-alcohol [5] | 0.10-7.0 | 0.50-6.5 | 1.0-6.0 | 1.5-5.0 |
| Anionic surfactant [6] | 0.10-7.0 | 0.10-5.0 | 0.15-4.0 | 0.20-3.5 |
| Non-ionic surfactant | 0.10-4.0 | 0.15-3.8 | 0.20-3.5 | 0.30-2.0 |
| Thickening agent [3] | 0.20-6.0 | 0.25-5.5 | 0.30-5.0 | 0.40-4.5 |
| Cosmetic carrier [1] | ad 100 | ad 100 | ad 100 | ad 100 |

|  | AF 17 | AF 18 | AF 19 | AF 20 |
| --- | --- | --- | --- | --- |
| Oxidizing agent [4] | 0.5-20 | 1.0-18 | 1.2-16 | 1.5-15 |
| $C_8$-$C_{30}$-alcohol [5] | 0.10-7.0 | 0.50-6.5 | 1.0-6.0 | 1.5-5.0 |
| Anionic surfactant [6] | 0.10-7.0 | 0.10-5.0 | 0.15-4.0 | 0.20-3.5 |
| Non-ionic surfactant [7] | 0.10-4.0 | 0.15-3.8 | 0.20-3.5 | 0.30-2.0 |
| Thickening agent [3] | 0.20-6.0 | 0.25-5.5 | 0.30-5.0 | 0.40-4.5 |

-continued

| Cosmetic carrier [1] | ad 100 | ad 100 | ad 100 | ad 100 |
|---|---|---|---|---|
| | AF 21 | AF 22 | AF 23 | AF 24 |
| Oxidizing agent [4] | 0.5-20 | 1.0-18 | 1.2-16 | 1.5-15 |
| $C_8$-$C_{30}$-alcohol [5] | 0.10-7.0 | 0.50-6.5 | 1.0-6.0 | 1.5-5.0 |
| Anionic surfactant [6] | 0.10-7.0 | 0.10-5.0 | 0.15-4.0 | 0.20-3.5 |
| Non-ionic surfactant [7] | 0.10-4.0 | 0.15-3.8 | 0.20-3.5 | 0.30-2.0 |
| Thickening agent [8] | 0.20-6.0 | 0.25-5.5 | 0.30-5.0 | 0.40-4.5 |
| Cosmetic carrier [1] | ad 100 | ad 100 | ad 100 | ad 100 |
| | AF 25 | AF 26 | AF 27 | AF 28 |
| Oxidizing agent [4] | 0.5-20 | 1.0-18 | 1.2-16 | 1.5-15 |
| $C_8$-$C_{30}$-alcohol [5] | 0.10-7.0 | 0.50-6.5 | 1.0-6.0 | 1.5-5.0 |
| Anionic surfactant [6] | 0.10-7.0 | 0.10-5.0 | 0.15-4.0 | 0.20-3.5 |
| Non-ionic surfactant [7] | 0.10-4.0 | 0.15-3.8 | 0.20-3.5 | 0.30-2.0 |
| Thickening agent [8] | 0.20-6.0 | 0.25-5.5 | 0.30-5.0 | 0.40-4.5 |
| Acid | 0.1-3.0 | 0.5-2.5 | 0.8-2.0 | 0.9-1.5 |
| Cosmetic carrier [1] | ad 100 | ad 100 | ad 100 | ad 100 |
| | AF 29 | AF 30 | AF 31 | AF 32 |
| Oxidizing agent [4] | 0.5-20 | 1.0-18 | 1.2-16 | 1.5-15 |
| $C_8$-$C_{30}$-alcohol [5] | 0.10-7.0 | 0.50-6.5 | 1.0-6.0 | 1.5-5.0 |
| Anionic surfactant [6] | 0.10-7.0 | 0.10-5.0 | 0.15-4.0 | 0.20-3.5 |
| Non-ionic surfactant [7] | 0.10-4.0 | 0.15-3.8 | 0.20-3.5 | 0.30-2.0 |
| Thickening agent [8] | 0.20-6.0 | 0.25-5.5 | 0.30-5.0 | 0.40-4.5 |
| Acid [9] | 0.1-3.0 | 0.5-2.5 | 0.8-2.0 | 0.9-1.5 |
| Cosmetic carrier [1] | ad 100 | ad 100 | ad 100 | ad 100 |

[1] aqueous or aqueous-alcoholic carrier
[2] selected from compounds of the formula $R(OCH_2CH_2)_n$—$OSO_3$—$X^+$, where R is saturated or unsaturated $C_8$-$C_{30}$-alkyl radicals, n is an integer from about 10 to about 50 and $X^+$ is a physiologically tolerated cation,
[3] selected from the group of copolymers of (meth)acrylic acid and (meth)acrylic esters, copolymers of (meth)acrylates and (meth)acrylamides, copolymers of hydroxyethyl (meth) acrylates and (meth)acrylamides, copolymers of (meth)acrylates, (meth)acrylamides and ethoxylated (meth)acrylic esters and mixtures thereof
[4] hydrogen peroxide, amount calculated on about 100% hydrogen peroxide,
[5] selected from a mixture of linear $C_{14}$-$C_{18}$-Alcohols, in particular cetearyl alcohol, and linear $C_{14}$-$C_{18}$-alcohols, in particular cetyl alcohol,
[6] selected from compounds of the formula $R(OCH_2CH_2)_n$—$OSO_3$—$X^+$, wherein R represents saturated or unsaturated $C_{12}$-$C_{20}$-Alkyl radicals, n represents integers from about 25 to about 35 and $X^+$ represents sodium, in particular sodium Coceth-30 sulphate,
[7] selected from ethoxylated alcohols having 14 to 18 carbon atoms and 20 to 30 ethylene oxide units per mole of alcohol, in particular Ceteareth-20
[8] selected from copolymers of (meth)acrylic acid and acrylic acid ethyl ester,
[9] a mixture of dipicolinic acid, disodium pyrophosphate and 1-hydroxyethane-1,1-diphosphonic acid.

The AF 1 to 32 versions described above are each packaged in packaging (VP) which has the arrangement of the multilayer film (F) described below (viewed from the interior (is in contact with the cosmetic formula (KM)) to the exterior):

a) *Interior*-Layer (P1)-Layer (P2)-Barrier layer (BS)-*Exterior*,
b) *Interior*-Layer (P1)-Barrier layer (BS)-Layer (P2)-*exterior*,
c) *Interior*-Layer (P2)-Layer (P1)-Barrier layer (BS)-*Exterior*,
d) *Interior*-Layer (P2)-Barrier layer (BS)-Layer (P1)-*Exterior*,
e) *Interior*-Barrier layer (BS)-Layer (P1)-Layer (P2)-*Exterior*,
f) *Interior*-Barrier layer (BS)-Layer (P2)-Layer (P1)-*Exterior*,
g) *Interior*-Layer (P1)-First adhesive layer (SK1)-Layer (P2)-Second adhesive layer (SK2)-Barrier Layer (BS)-*Exterior*,
h) *Interior*-Layer (P1)-Adhesive Layer (SK1)-Layer (P2)-Barrier Layer (BS)-*Exterior*,
i) *Interior*-Layer (P1)-Layer (P2)-Second adhesive layer (SK2)-Barrier layer (BS)-*Exterior*,
j) *Interior*-Barrier layer (BS)-First adhesive layer (SK1)-Layer (P1)-Second adhesive layer (SK2)-Layer (P2)-*Exterior*,
k) *Interior*-Barrier layer (BS)-Adhesive Layer (SK)-Layer (P1)-Layer (P2)-*Exterior*,
l) *Interior*-Barrier layer(BS)-Layer (S1)-Adhesive Layer (SK)-Layer (P2)-*Exterior*,
m) *Interior*-Layer (P1)-First adhesive layer (SK1)-Barrier layer (BS)-Second adhesive layer (SK2)-Layer (P2)-*Exterior*,
n) *Interior*-Layer (P1)-Adhesive Layer (SK)-Barrier layer (BS)-Layer (P2)-*Exterior*,
o) *Interior*-Layer (P1)-Barrier layer (BS)-Adhesive layer (SK)-Layer (P2)-*Exterior*.

The inventive products obtained in this way have a high storage stability and a water loss during storage that is within the acceptable range. No swelling or delamination of the packaging (VP) was observed during storage of these cosmetic products as contemplated herein.

The product as contemplated herein is used for the purpose of oxidative colour change. For this purpose, the preparation (KM) packed in the packaging (VP), which is the oxidizing agent preparation, is mixed with at least one other preparation (B) to produce the ready-to-use colour-changing agent. To prevent incompatibilities or to avoid a premature reaction, the preparations (KM) and (B) are made up separately.

A particularly preferred product as contemplated herein comprises a preparation (B) made up separately from the preparation (KM), the preparation (B) containing at least one compound selected from oxidation dye precursors, direct dyes, alkalising agents and mixtures thereof. Preferred products of the present disclosure additionally comprises at least one second cosmetic composition (KM2) which contains at least one compound selected from oxidation dye precursors, direct dyes, alkalising agents and mixtures thereof and which is packaged separately from the cosmetic composition (KM).

If oxidation dyeing is desired, the preparation (B) contains at least one oxidation dye precursor. Oxidation dye precursors can be divided into developers and couplers. Due to their greater sensitivity to oxygen, developers are usually used in the form of their physiologically compatible salts (e.g. in the form of their hydrochlorides, hydrobromides, hydrogen sulphates or sulphates). Coupler components alone do not form a significant colouration in the course of oxidative dyeing, but always require the presence of developer components. Coupler components alone do not form a significant colouration in the course of oxidative dyeing, but always require the presence of developer components. Particularly suitable developer-type oxidation dye precursors are selected from at least one compound from the group formed by p-phenylenediamine, p-toluenediamine, 2-(2-hydroxyethyl)-p-phenylenediamine, 2-(1,2-dihydroxyethyl)-p-phenylenediamine, N,N-to-(2-hydroxyethyl)-p-phenylenediamine, 2-methoxymethyl-p-phenylenediamine, N-(4-amino-3-methylphenyl)-N-[3-(1H-imidazol-1-y1)propyl] amine, N,N'-to-(2-hydroxyethyl)-N,N'-to-(4-aminophenyl)-1,3-diamino-propane-2-ol, to-(2-hydroxy-5-aminophenyl) methane, 1.3-to-(2.5-diaminophenoxy)propane-2-ol, N,N'-to-(4-aminophenyl)-1,4-diazacycloheptane, 1,10-to-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one and their physiologically compatible salts.

Particularly suitable oxidation dye precursors of the coupler type are selected from the group including 3-aminophenol, 5-amino-2-methylphenol, 3-amino-2-chloro-6-methylphenol, 2-hydroxy-4-aminophenoxyethanol, 5-Amino-4-chloro-2-methylphenol, 5-(2-hydroxyethyl) amino-2-methylphenol, 2,4-dichloro-3-aminophenol, 2-aminophenol, 3-phenylenediamine, 2-(2,4-diaminophenoxy) ethanol, 1,3-bis (2,4-diaminophenoxy) propane, 1-methoxy-2-amino-4-(2-hydroxyethylamino) benzene, 1,3-bis (2,4-diaminophenyl) propane, 2,6-bis(2'-hydroxyethylamino)-1-methylbenzene, 2-({3-[(2-hydroxyethyl) amino]-4-methoxy-5-methylphenyl}amino) ethanol, 2-({3-[(2nd-Hydroxyethyl) amino]-2-methoxy-5-methylphenyl}amino) ethanol, 2-({3-[(2-hydroxyethyl) amino]-4,5-dimethylphenyl}amino) ethanol, 2-[3-morpholine-4-ylphenyl) amino]ethanol, 3-amino-4-(2-methoxyethoxy)-5-methylphenylamine, 1-amino-3-bis (2-hydroxyethyl) aminobenzene, resorcinol, 2-methylresorcinol, 4-chlororesorcinol, 1,2,4-Trihydroxybenzene, 2-Amino-3-Hydroxypyridine, 3-Amino-2-methyl amino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-Dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or their physiological tolerable salts.

In addition, the preparation (B) may also contain one or more direct dyes. Suitable non-ionic direct dyes can be selected from the group of HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-to-(2-hydroxyethyl)-amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl) amino]-3-nitrophenol, 4-nitro-o-phenylenediamine, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

Suitable anionic direct dyes can be selected from the group of Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol Blue and Tetrabromophenol Blue.

Suitable cationic direct dyes are cationic triphenylmethane dyes, such as Basic Blue 7, Basic Blue 26, Basic Violet 2 and Basic Violet 14, aromatic systems substituted with a quaternary nitrogen group, such as Basic Yellow 57, Basic Red 76, Basic Blue 99, Basic Brown 16 and Basic Brown 17, cationic anthraquinone dyes such as HC Blue 16 (Bluequat B) and direct dyes containing a heterocycle containing at least one quaternary nitrogen atom, in particular Basic Yellow 87, Basic Orange 31 and Basic Red 51. The cationic direct dyes marketed under the trade mark Arianor are also suitable cationic direct dyes as contemplated herein.

Dyeing processes on keratin fibres usually take place in an alkaline environment. To protect the keratin fibres and also the skin as much as possible, the adjustment of a too high pH-value is however not desirable. It is therefore preferable if the pH of agent (B) is between about 7 and about 11, in particular between about 8 and about 10.5. The pH values for the purposes of the present disclosure are pH values measured at a temperature of 22° C.

The preparation (B) may contain at least one alkalising agent. The alkalising agents usable for adjusting the preferred pH value as contemplated herein can be selected from the group formed by ammonia, alkanolamines, basic amino acids, as well as inorganic alkalising agents such as (earth) alkali metal hydroxides, (earth)alkali metal metasilicates, (earth)alkali metal phosphates and (earth)alkali metal hydrogen phosphates. Preferred inorganic alkalising agents are magnesium carbonate, sodium hydroxide, potassium hydroxide, sodium silicate and sodium metasilicate. Organic alkalising agents usable as contemplated herein are preferably selected from monoethanolamine, 2-amino-2-methylpropanol and triethanolamine. The basic amino acids usable as alkalising agents as contemplated herein are preferably selected from the group formed by arginine, lysine, ornithine and histidine, especially preferably arginine. However, in the course of the examination of the present disclosure it turned out that, as contemplated herein, preferred agents are still exemplified by the fact that they additionally contain an organic alkalising agent. An embodiment of the first object of present disclosure is exemplified in that the agent additionally contains at least one alkalising agent selected from the group formed by ammonia, alkanolamines and basic amino acids, in particular ammonia, monoethanolamine and arginine or its compatible salts.

The preparation (B) can also contain additional active ingredients, auxiliaries and additives. For example, it may contain one or more fat components from the group of $C_{12}$-$C_{30}$-fatty alcohols $C_{12}$-$C_{30}$-fatty acid triglycerides, $C_{12}$-$C_{30}$-fatty acid monoglycerides, $C_{12}$-$C_{30}$-fatty acid diglycerides and/or hydrocarbons.

Preferably, an additional surface-active substance may be added to the preparation (B), such surface-active substances being referred to as surfactants or emulsifiers depending on the field of application: They are preferably selected from anionic, zwitterionic, amphoteric and non-ionic surfactants and emulsifiers.

Preferably, the preparation (B) contains at least one anionic surfactant. Preferred anionic surfactants are fatty acids, alkyl sulphates, alkyl ether sulphates and ether carboxylic acids with 10 to 20 C atoms in the alkyl group and up to 16 glycol ether groups in the molecule.

Furthermore, the preparation (B) may additionally contain at least one zwitterionic surfactant. Preferred zwitterionic surfactants are betaines, N-alkyl-N,N-dimethylammonium glycinate, N-Acyl aminopropyl-N,N-dimethylammonium glycinate, and 2-alkyl-3-carboxymethyl-3-hydroxyethyl-imidazolines. A preferred zwitterionic surfactant is known under the INCI name cocamidopropyl betaine.

In addition, the preparation (B) may be intended to contain at least one amphoteric surfactant. Preferred amphoteric surfactants are N-alkylglycines, N-alkylpropionic acids, N-alkylaminobutyric acids, N-alkyliminodipropionic acids, N-aydroxyethyl-N-alkylamidopropylglycines, N-alkyltaurines, N-alkylsarcosines, 2-alkylaminopropionic acids and alkylaminoacetic acids. Particularly preferred amphoteric surfactants are N-cocoalkylaminopropionate, as cocoacylaminoethylaminopropionate and C12-C18-acylsarcosine.

It has also proven to be advantageous if the preparation (B) contains further, non-ionic, surface-active substances. Preferred non-ionic surfactants are alkyl polyglycosides and alkylene oxide adducts to fatty alcohols and fatty acids with 2 to 30 mol ethylene oxide per mol fatty alcohol or fatty acid. Preparations with excellent properties are also obtained if they contain fatty acid esters of ethoxylated glycerol as non-ionic surfactants.

The non-ionic, zwitterionic or amphoteric surfactants are used in proportions of from about 0.1 to about 45% by weight, preferably from about 1 to about 30% by weight and very preferably from about 1 to about 15% by weight, based on the total weight of the preparation (B).

The preparation (B) may also contain at least one thickener. There are no restrictions in principle with regard to these thickening agents. Both organic and purely inorganic thickeners can be used. Suitable thickeners are anionic, synthetic polymers, cationic, synthetic polymers, naturally occurring thickeners such as non-ionic guargum, scleroglucangum or xanthangum, gum arabic, ghatti gum, karaya gum, tragacanth gum, carrageenan gum, agar-agar, Locust bean gum, pectins, alginates, starch fractions and derivatives such as amylose, amylopectin and dextrins, and cellulose derivatives such as methyl cellulose, carboxyalkyl celluloses and hydroxyalkyl celluloses, non-ionic, fully synthetic polymers such as polyvinyl alcohol or polyvinyl pyrrolidinone; as well as inorganic thickening agents, in particular layer silicates such as bentonite, in particular smectites such as montmorillonite or hectorite.

Furthermore, the preparation (B) may contain other active substances, auxiliaries and additives, such as non-ionic polymers such as vinylpyrrolidinone/vinyl acrylate copolymers, polyvinylpyrrolidinone, vinylpyrrolidinone/vinyl acetate copolymers, polyethylene glycols and polysiloxanes; additional silicones such as volatile or non-volatile, straight-chain, branched or cyclic, crosslinked or non-crosslinked polyalkylsiloxanes (such as dimethicones or cyclomethicones), polyarylsiloxanes and/or polyalkylarylsiloxanes, in particular polysiloxanes having organofunctional groups, such as substituted or unsubstituted amines (amodimethicones), carboxyl, alkoxy and/or hydroxyl groups (dimethicone copolymers), linear polysiloxane (A)-polyoxyalkylene (B) block copolymers, grafted silicone polymers; cationic polymers such as quaternized cellulose ethers, polysiloxanes having quaternary groups, dimethyldiallylammonium chloride polymers, acrylamide dimethyldiallyl ammonium chloride copolymers, diethyl sulphate quaternized dimethyl-amino-ethylmethacrylate-vinylpyrrolidinone copolymers, vinylpyrrolidinone-imidazolinium methochloride copolymers and quaternized polyvinyl alcohol; zwitterionic and amphoteric polymers anionic polymers such as polyacrylic acids or cross-linked polyacrylic acids; structural agents such as glucose, maleic acid and lactic acid; hair conditioning compounds such as phospholipids, for example lecithin and cephalins; perfume oils, dimethylisosorbide and cyclodextrins; fibre structure-improving active substances, in particular mono-, di- and oligosaccharides such as glucose, galactose, fructose, fructose and lactose; dyes for colouring the composition; anti-dandruff active substances such as piroctone olamine, zinc omadine and climbazol; amino acids and oligopeptides; protein hydrolysates on an animal and/or vegetable basis, as well as in the form of their fatty acid condensation products or optionally anionically or cationically modified derivatives; fatty substances and vegetable oils; light stabilizers and UV-blockers; active ingredients such as panthenol, pantothenic acid, pantolactone, allantoin, pyrrolidinonecarboxylic acids and their salts as well as bisabolol; polyphenols, in particular hydroxycinnamic acids, 6,7-dihydroxycumarins, hydroxybenzoic acids, catechins, tannins, leucoanthocyanidins, Anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling and penetrating agents such as glycerol, propylene glycol monoethyl ether, carbonates, hydrogen carbonates, guanidines, ureas as well as primary, secondary and tertiary phosphates; opacifiers such as latex, styrene/PVP and styrene/acrylamide copolymers; pearlescent agents such as ethylene glycol mono- and distearate and PEG-3 distearate as well as pigments.

The selection of these additional substances will be made by the expert according to the desired properties of the preparation (B) as well as the product as contemplated herein. With regard to other optional components and the quantities of these components used, explicit reference is made to the relevant manuals known to the specialist. The additional active substances and auxiliaries are preferably used in the preparation (B) in quantities of from about 0.0001 to about 25% by weight each, in particular from about 0.0005 to about 15% by weight each, based on the total weight of the preparation (B).

The following examples explain the present disclosure without limiting it:

EXAMPLES

A 100 nm thick layer of silicon dioxide SiOx was evaporated onto a film layer of polyethylene terephthalate with a thickness of 40 μm (micrometer). The SiOx layer was then painted over with approx. 3 g/m² ORMOCER polymer and cured. A 70 μm (micrometer) thick layer of polyethylene was then applied to the ORMOCER layer. A packaging (VP) was produced from the film.

The following cosmetic compositions (KM) were used (all figures in % by weight):

| Ingredients | KM |
| --- | --- |
| Sodium hydroxide (50%) | 0.72 |
| Dipicolinic acid | 0.10 |
| Disodium pyrophosphate | 0.030 |
| 1-hydroxyethane-1,1-diphosphonic acid (60%) | 1.5 |
| Oxidizing agent [1] | 10 |
| $C_8$-$C_{30}$-alcohol [2] | 3.5 |
| Anionic surfactant [3] | 2.5 |
| Non-ionic surfactant [4] | 1.0 |
| Thickening agent [5] | 10 |
| Water | ad 100 |

[1] preferably hydrogen peroxide, calculated on 100% $H_2O_2$,
[2] preferably a linear $C_{14}$-$C_{18}$-alcohol, especially cetyl alcohol
[3] preferably a sodium salt of $C_{16}$-$C_{18}$-alkysulphates substituted with oxyethylene groups, especially Disponil ® FES 77,
[4] preferable a $C_{16}$-$C_{18}$-Alkyl ether substituted with oxyethylene, especially ceteareth-20,
[5] preferably a copolymer of (meth)acrylic acid and acrylic acid ethyl ester, especially aculyn 33 A

| Ingredients | KM |
| --- | --- |
| Ammonia (25% ig) | 0.65 |
| Dipicolinic acid | 0.10 |
| Disodium pyrophosphate | 0.030 |
| 1-hydroxyethane-1,1-diphosphonic acid (60%) | 1.5 |
| Oxidizing agent [1] | 12 |
| $C_8$-$C_{30}$-alcohol [2] | 3.5 |
| Anionic surfactant [3] | 2.5 |
| Non-ionic surfactant [4] | 1.0 |

-continued

| Ingredients | KM |
|---|---|
| Thickening agent [5] | 10 |
| Water | ad 100 |

[1] preferably hydrogen peroxide, calculated on 100% $H_2O_2$,
[2] preferably a linear $C_{14}$-$C_{18}$-alcohol, especially cetyl alcohol
[3] preferably a sodium salt of $C_{16}$-$C_{18}$-alkysulphates substituted with oxyethylene groups, especially Disponil ® FES 77,
[4] preferably a $C_{16}$-$C_{18}$-Alkyl ether substituted with oxyethylene, especially ceteareth-20,,
[5] preferably a copolymer of (meth)acrylic acid and Acrylic acid ethyl ester, especially aculyn 33 A The cosmetic composition KM filled into the previously described packaging (VP). The packages were then stored at 40° C. for 24 weeks. The packaging was not inflated or delaminated.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Cosmetic product for modifying the natural colour of keratinous fibres comprising
 (i) at least one packaging (VP) comprising at least one multilayer film (F) which comprises at least a first polymer layer (P1), at least a second polymer layer (P2) and at least one barrier layer (BS), and
 (ii) at least one cosmetic composition (KM), which is packed in the packaging (VP) and comprises:
  a) at least one oxidizing compound,
  b) at least one $C_8$-$C_{30}$ alcohol,
  c) at least one anionic surfactant, selected from compounds of the formula $R(OCH_2CH_2)_n\text{---}OSO_3\text{---}X^+$, where R is saturated or unsaturated $C_8$-$C_{30}$-alkyl radical, n is an integer from 10 to 50 and $X^+$ is a physiologically acceptable cation,
  d) at least one nonionic surfactant and
  e) at least one thickener selected from the group of copolymers of (meth) acrylic acid and (meth) acrylic acid esters, copolymers of (meth) acrylates and (meth) acrylamides, copolymers of hydroxyethyl (meth) acrylates and (meth) acrylamides, and copolymers of (meth) acrylates, (meth) acrylamides and ethoxylated (meth) acrylic esters,
  wherein the first polymer layer (P1) comprises polyethylene terephthalate or polyethylene naphthalate; the second polymer layer (P2) comprises a polyolefin; and the barrier layer (BS) comprises a polyester provided with a silicon dioxide layer.

2. The cosmetic product according to claim 1, wherein the thickener comprises a copolymer of (meth)acrylic acid and acrylic acid ethyl esters.

3. The cosmetic product according to claim 1, wherein the barrier layer (BS) comprises polyethylene terephthalate.

4. The cosmetic product according to claim 1, wherein the first polymer layer (P1) has a layer thickness of about 4 µm to about 50 µm; the second polymer layer (P2) has a layer thickness of about 20 µm to about 150 µm; and the barrier layer (BS) has a layer thickness of about 4 µm to about 20 µm.

5. The cosmetic product according to claim 1, wherein the first polymer layer (P1) has a layer thickness of about 6 µm to about 20 µm; the second polymer layer (P2) has a layer thickness of about 40 µm to about 90 µm; and the barrier layer (BS) has a layer thickness of about 6 µm to about 15 µm.

6. The cosmetic product according to claim 1, wherein the multilayer film (F) has an oxygen transmission rate at 23° C. and 50% relative humidity of 0.1 to 5 $cc/m^2/d/bar$, and has a water vapour permeability at 38° C. and 100% relative humidity of from 0.1 to 5 $g/m^2d$.

7. The cosmetic product according to claim 1, wherein the multilayer film (F) has an oxygen transmission rate at 23° C. and 50% relative humidity of 0.5 to 2.5 $cc/m^2/d/bar$, and has a water vapour permeability at 38° C. and 100% relative humidity of from 0.5 to 2.5 $g/m^2d$.

8. The cosmetic product according to claim 1, wherein the multilayer film (F) has an adhesive strength of from 0.1 to 10 N/15 mm; and wherein the packaging (VP) has a seal strength of from 10 to 40 N/15 mm under the conditions 150° C., 2.54 cm (1") and 4 $kg/cm^2$.

9. The cosmetic product according claim 1, wherein the at least one multilayer film (F) comprises the at least one barrier layer (BS) between the at least one first polymer layer (P1) and the at least one second polymer layer (P2).

10. The cosmetic product according to claim 1, wherein the first polymer layer (P1) forms an outer layer of the film (F).

11. The cosmetic product according to claim 1, wherein the cosmetic composition (KM) has a pH measured at 20° C. of 1.5 to 5.0.

12. The cosmetic product according to claim 11, where the pH is 2.5 to 4.

13. The cosmetic product according to claim 1, wherein the cosmetic composition comprises at least one oxidizing compound in a total amount of 0.5 to 20% by weight; and wherein the cosmetic composition comprises the at least one $C_8$-$C_{30}$-alcohol in a total amount of 0.10 to 7.0% by weight. %, based on the total weight of the cosmetic composition (KM).

14. Cosmetic product according to claim 1, wherein the anionic surfactant c) of the cosmetic composition is a sodium sulphate of a linear $C_{12}$-$C_{14}$-alkyl ethoxylate with 30 ethylene oxide units per surfactant molecule, and the nonionic surfactant d) of the cosmetic composition is a linear $C_{16}$-$C_{18}$ ethoxylated alcohol with 20 ethylene oxide units per surfactant molecule; an wherein the anionic surfactant is present in an amount of 1 to 3-% by weight, and the nonionic surfactant is present in the cosmetic composition in an amount of 0.5 to 2-% by weight, based on the total weight of the cosmetic composition.

15. A multilayer film (F) comprising a first polymer layer (P1), a second polymer layer (P2) and a barrier layer (BS), wherein the first polymer comprises polyethylene terephthalate or polyethylene naphthalate, the second polymer layer (P2) comprises a polyolefin, and the barrier layer (BS) comprises a polyester provided with a silicon dioxide layer.

16. A packaging for containing a cosmetic composition comprising the film of claim 15, wherein the first polymer layer (P1) forms an interior layer.

17. A packaging for containing a cosmetic composition comprising the film of claim 15, wherein the second polymer layer (P2) forms an interior layer.

18. A packaging for containing a cosmetic composition comprising the film of claim 15, wherein the barrier layer (BS) forms an interior layer.

19. A packaging comprising the film of claim 15, and containing a cosmetic composition comprising about 9 to about 12% hydrogen peroxide.

* * * * *